US006679912B2

(12) United States Patent
Stelter

(10) Patent No.: US 6,679,912 B2
(45) Date of Patent: Jan. 20, 2004

(54) BREAST PROSTHESIS

(75) Inventor: Nils Stelter, Achenmühle (DE)

(73) Assignee: Amoena Medizin-Orthopadie-Technik GmbH & Co., Raubling (DE)

( * ) Notice: Subject to any disclaimer, the term of this patent is extended or adjusted under 35 U.S.C. 154(b) by 0 days.

(21) Appl. No.: 10/057,814

(22) Filed: Jan. 23, 2002

(65) Prior Publication Data

US 2002/0103539 A1 Aug. 1, 2002

(51) Int. Cl.$^7$ .................................................. A61F 2/12
(52) U.S. Cl. ........................................................ 623/7
(58) Field of Search ...................... 623/7, 8, 11; 528/26, 528/32

(56) References Cited

U.S. PATENT DOCUMENTS

| | | | | |
|---|---|---|---|---|
| 3,075,529 A | | 1/1963 | Young, Jr. ................. 128/403 |
| 4,208,506 A | * | 6/1980 | Deichert et al. ............... 528/32 |
| 4,277,595 A | * | 7/1981 | Deichert et al. ............... 528/26 |
| 4,856,294 A | | 8/1989 | Scaringe et al. ............ 62/259.3 |
| 4,964,402 A | | 10/1990 | Grim et al. ................ 128/80 H |
| 5,106,520 A | | 4/1992 | Salyer .......................... 252/70 |
| 5,415,222 A | | 5/1995 | Colvin et al. .................. 165/46 |
| 5,851,338 A | | 12/1998 | Pushaw ...................... 156/278 |
| 6,171,594 B1 | * | 1/2001 | Nielsen ...................... 424/744 |

FOREIGN PATENT DOCUMENTS

| | | | |
|---|---|---|---|
| DE | 27 01 627 A1 | 7/1978 | ............. A61F/1/00 |
| DE | 44 21 516 C1 | 7/1995 | ............. A61F/2/52 |
| EP | 0 392 960 | 10/1990 | ............. A61F/2/52 |
| EP | 0 768 068 A1 | 4/1997 | ............. A61F/2/52 |

* cited by examiner

Primary Examiner—David J. Isabella
(74) Attorney, Agent, or Firm—Needle & Rosenberg, P.C.

(57) ABSTRACT

Disclosed is a breast prosthesis comprised of at least one layer and formed to imitate the shape of a breast, the at least one layer being welded in a plastic film, comprised of a phase change material having a phase change temperature approximate the user's body temperature.

16 Claims, 3 Drawing Sheets

BREAST PROSTHESIS

This application claims priority to German Utility Model Application No, 201 01 174.3, filed Jan. 23, 2001 in the German Patent Office.

FIELD OF THE INVENTION

The invention relates in general to a breast prosthesis. More particularly, the invention relates to a breast prosthesis comprised of at least two bodies formed to imitate the shape of a breast, the bodies being welded in at least one plastic film and formed of an addition-vulcanized two-component silicone rubber mass, and in which that portion of the prosthesis facing toward or received against the body of the user is comprised at least in part of a temperature phase change material having a phase change temperature approximately that of the user's body temperature.

BACKGROUND OF THE INVENTION

A method is known, for example, from DE 27 01 672 for the manufacture of breast prostheses from shell-shaped bodies which are formed to imitate the shape of the breast. The bodies comprising the prosthesis are welded in plastic films and are made from an addition-vulcanized two-component silicone rubber mass. The prosthetic breasts manufactured by this method are formed to imitate the shape of the natural breast in almost ideal manner in that the appearance and the behavior of the prostheses mimic a natural breast due to the elastic softness, the movability, the consistence and the weight of the material used in the prostheses.

The breast prosthesis is secured to the breast of the wearer to be as unslippable as possible thereon. For this purpose, it is known, for example from EP 392 960, to provide a breast prosthesis of the type described above, which is provided with a circumferential, lip-like border area on its rear side with a circumferential shoulder which is formed by a step and on which adhesive strips or adhesive pieces are secured which interact with the adhesive regions or strips secured to the body of the woman by a hypo-allergenic adhesive such that the prosthesis is connected to the adhesive strips adhering to the skin and can be released from these again. A hook-and-loop fastener is, for example, provided as the securing means in this connection.

Particularly when the breast prosthesis is secured in accordance with its intended purpose properly and in a manner as unslippable as possible to the breast of the wearer, the problem of an unpleasant accumulation of heat often occurs under the prosthesis. The reasons for this are the deficient ventilation and the poor heat transport of the plastic materials of the prosthesis used. In order to improve the comfort in wear, it is, for example, known from DE 44 21 516 C1 to provide a breast prosthesis with a textile rear side in which a cavity between the textile rear side and the prosthesis consisting of plastic can be filled in with cotton wool. However, this solution does not result in the desired comfort in wear, either.

SUMMARY OF THE INVENTION

The invention here comprises a breast prosthesis at least partially comprised of, at least on its side or surface facing or received against the user's body, a phase change material ("PCM"). The PCM will have a phase changing temperature in the region of, i.e., approximate, a person's body temperature. During a phase change, for example from a solid state to a liquid state or from the liquid state to a vapor phase, the PCM material is capable of absorbing a certain amount of heat at a constant temperature. This amount of heat is also termed latent heat. On the reverse phase change from a vapor to a fluid or from a fluid to a solid, the stored latent heat is emitted, again at a constant temperature. In this regard these heat storing materials are characterized in that they do not require any large temperature differences to store large amounts of heat therein, for example during the storage process as a latent heat store, unlike hot water tanks.

For this reason, this phase change material is ideally suited to absorb the heat occurring below the prosthesis during the accumulation of heat at the same temperature, or to give back this stored heat again at the same temperature when the ambient temperature falls.

It is, therefore, an object of the invention to provide an improved breast prosthesis such that the discomfort in wear is largely suppressed by avoiding the heat accumulation between the prosthesis and the skin of the wearer.

This object is solved by providing a breast prosthesis comprised of at least one body formed to imitate the shape of a breast, the body being welded in at least one plastic film and formed of an addition-vulcanized two-component silicone rubber mass, and in which that portion of the prosthesis facing toward or received against the body of the user is comprised at least in part of a phase change material having a phase change temperature approximately that of the user's body temperature.

The entire breast prosthesis can be comprised of a largely homogeneous layer in which the PCM material is mixed in with the silicone rubber mass. Alternately, the breast prosthesis can be made as a multi-layer prosthesis, preferably a two-layer prosthesis, with the PCM material only being mixed into the layer to be placed next to the body and where the layer of the prosthesis remote from the body can comprise a conventional addition-vulcanized two-component silicone rubber. The layer of the prosthesis to be placed next to the body may comprise a silicone oil or other thixotropically set liquids, a vulcanized silicone rubber, or a silicone foam into which the PCM material is embedded in each case.

In yet anther embodiment, the PCM material may be formed as a slab which is secured on the side of the prosthesis facing the body. In this regard, an air cushion can be formed between the slab-like PCM material and the prosthesis, the air cushion being capable of resulting in a better exchange of air, on the one hand, and in improved comfort in wear, on the other hand.

The PCM material can advantageously comprise a paraffin substance with a melting range of from approximately 33° C. to 37° C. The so-called heat paraffins used as the PCM material are paraffins especially modified for technical heat applications. These heat paraffins have a specific melting heat or melting enthalpy which is very high for organic substances at 108 kJ/kg to 250 kJ/kg.

BRIEF DESCRIPTION OF THE DRAWINGS

Further details and advantages of the invention result from the embodiments shown in the drawings.

DETAILED DESCRIPTION

Figure 1:
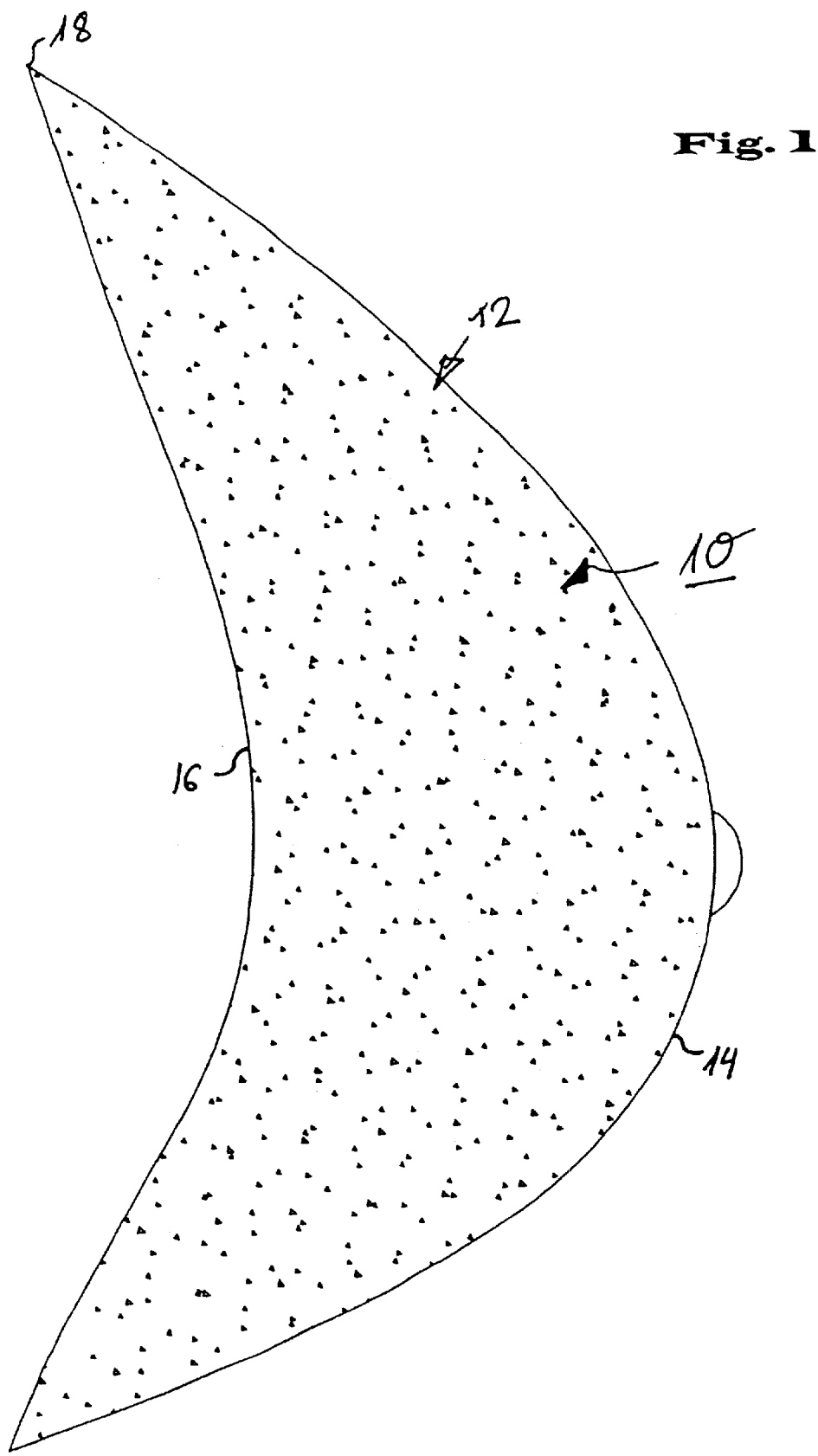
FIG. 1 is a longitudinal section through a breast prosthesis in accordance with a first embodiment of the present invention.

The breast prosthesis 10 shown in FIG. 1 is comprised of a shell-shaped body 12 made of an addition-vulcanized, resiliently elastically set two-component silicone rubber mass whose outside is covered by a polyurethane film 14 and whose inside is covered by a polyurethane film 16, each of which is connected to the other along a common circumferential rim 18 by a circumferential weld. In the embodiment shown here, so-called heat paraffins, i.e., phase change materials ("PCM"), are contained in an evenly distributed manner in the two-component silicone rubber mass. The melting range of the heat paraffin selected here will be in the range of from approximately 33° C. to approximately 37° C. These heat paraffins have a specific melting heat or melting enthalpy which is very high for organic substances at 108 kJ/kg to 250 kJ/kg.

Accordingly, if the skin surface temperature increases to this level, the PCM material is melted. A correspondingly large amount of melting energy is required for this which is led away from the skin surface as heat and causes a pleasant cooling effect here. If the skin surface temperature falls below the melting temperature of the heat paraffin at a later time, the material gives off the energy, i.e., the latent heat, during solidification of the material. The temperature fluctuations are thus restricted in a small range and effect a substantially enhanced comfort in wear.

Figure 2:
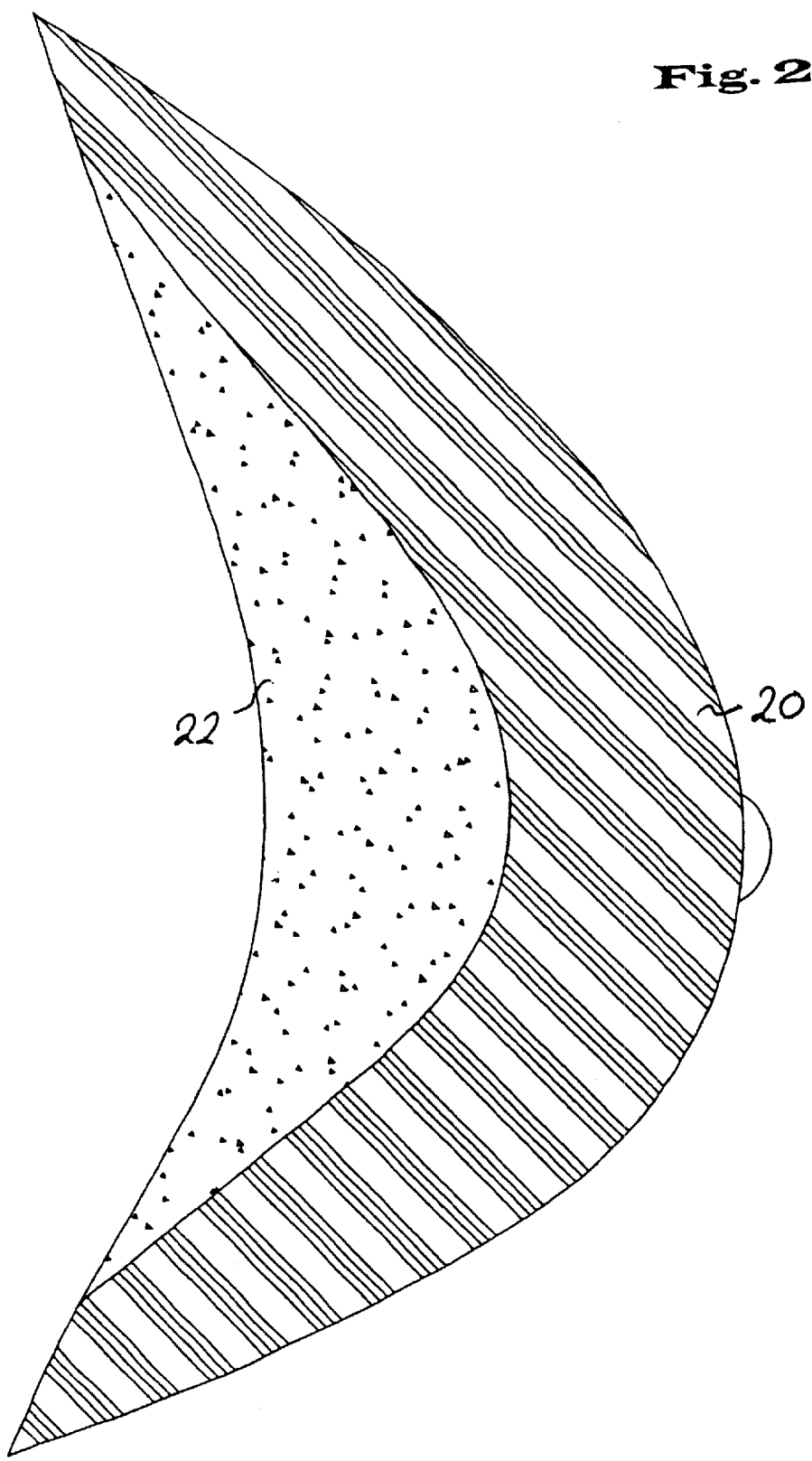
FIG. 2 is a longitudinal section through a breast prosthesis in accordance with a second embodiment of the present invention.

A breast prosthesis formed as a two-layer prosthesis is illustrated in FIG. 2. The outer layer or body 20 is comprised of a conventional addition-vulcanized two-component silicone rubber, that is of a standard silicone. It can alternatively be comprised of a so-called "light" silicone, which is an addition-vulcanized two-component silicone rubber into which a component lowering the specific weight of the mass is mixed. The inner layer or body 22, which faces the body of the wearer, is comprised of the phase change material. The phase change material can be present in an encapsulated form, or also in a pure form as a wax. It can also be embedded in a silicone oil, or any other, preferably a thixotropic material, liquids, a vulcanized silicon, or in a foam.

Figure 3:
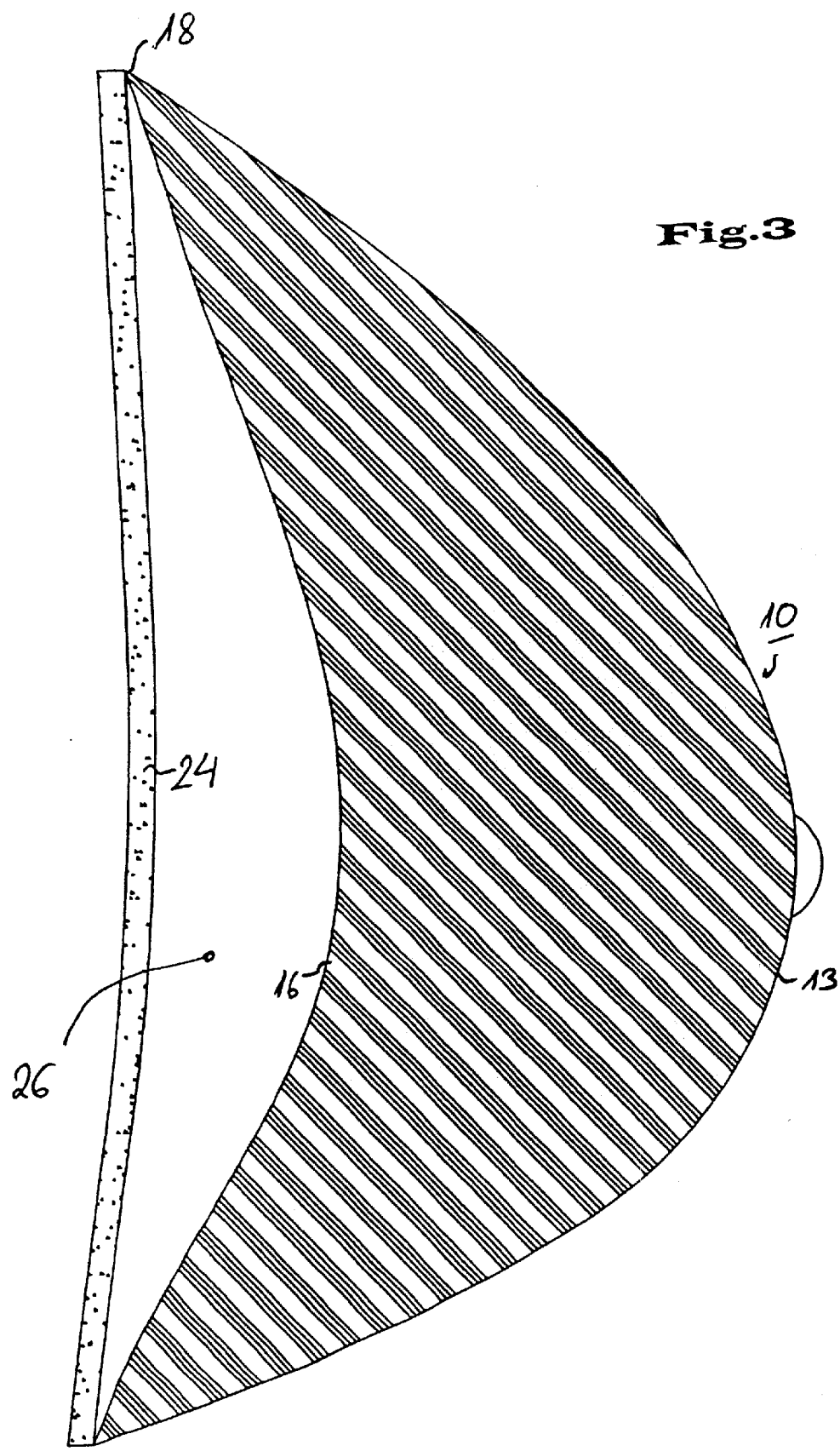
FIG. 3 is a longitudinal section through a breast prosthesis in accordance with a third embodiment of the present invention.

FIG. 3 illustrates an alternate embodiment of the breast prosthesis. Here a conventional breast prosthesis 10 is shown of a single chamber or body design as generally illustrated in FIG. 1. The breast prosthesis 10 of FIG. 3, however, is filled with a conventional addition-vulcanized two-component silicone rubber. On the side of the breast prosthesis 10 facing the wearer, a cooling layer 24 formed as a slab is arranged which is preferably adhered or welded to the prosthesis on or in the region of the circumferential rim 18 of the plastic films 13 and 16. An air cushion 26 is formed between the slab-like cooling layer 24 and the plastic film 16.

The slab-like cooling layer or slab 24 comprises a textile with an integrated PCM material such as is marketed by the company of Schoeller, under the name of "Comfortemp." The air cushion 26 provides the user with enhanced comfort in wear. The slab 24 can alternatively comprise a pad with PCM material therein as a replacement variant. For this purpose, the flexibly designed slab 24 is releasably connected in known manner to the remaining portion of the prosthesis in the region of the circumferential rim 18.

I claim:

1. A breast prosthesis comprised of at least one layer and formed to imitate the shape of a breast, the at least one layer being welded in a plastic film, wherein a side of the prosthesis adapted to face the body of the user is at least partially comprised of a phase change material having a phase change temperature approximate the user's body temperature, and wherein the phase change material is sized and shaped as a slab positioned within a pouch formed in the prosthesis, the pouch being secured to a side of the prosthesis adapted to face the body of the user.

2. The breast prosthesis of claim 1, wherein the at least one layer of the prosthesis is formed as an addition-vulcanized two-component silicone rubber mass.

3. The breast prosthesis of claim 1, wherein the prosthesis is comprised of a single layer, and wherein the single layer comprises the phase change material.

4. The breast prosthesis of claim 3, wherein the single layer is comprised of a silicone rubber.

5. The breast prosthesis of claim 1, wherein the prosthesis is comprised of two layers, and wherein the phase change material is mixed into a first layer of the prosthesis adapted to face the body of the user.

6. The breast prosthesis of claim 5, wherein the phase change material is embedded in a material selected from one of the group of materials comprising a silicone oil, a thixotropic material, a liquid, a vulcanized silicone rubber, or a silicone foam.

7. The breast prosthesis of claim 1, wherein the phase change material is sized and shaped as a slab, said slab being secured to a side of the prosthesis adapted to face the body of the user.

8. The breast prosthesis of claim 7, wherein the slab comprises a mixture of the phase change material and a textile material.

9. The breast prosthesis of claim 1, wherein the phase change material comprises a paraffin.

10. The breast prosthesis of claim 9, wherein the paraffin is encapsulated.

11. The breast prosthesis of claim 9, wherein the paraffin is uniformly embedded in a thixotropic material.

12. The breast prosthesis of claim 9, wherein the paraffin is pure.

13. The breast prosthesis of claim 12, wherein the paraffin is used as a wax.

14. A breast prosthesis comprised of a first layer and a second layer, each said layer being comprised of a silicone rubber welded in and covered by a plastic film, the first layer of the prosthesis being adapted to face the body of the user and at least partially comprised of a phase change material having a phase change temperature approximate the user's body temperature.

15. A breast prosthesis comprised of a single layer of a silicone rubber material welded in a plastic film, wherein the single layer further comprises a phase change material, the phase change material having a phase change temperature approximate the user's body temperature.

16. A breast prosthesis comprised of at least one layer and formed to imitate the shape of a breast, the at least one layer being welded in a plastic film, wherein a side of the prosthesis adapted to face the body of the user is at least partially comprised of a phase change material having a phase change temperature approximate the user's body temperature, and wherein the phase change material is sized and shaped as a slab secured to a side of the prosthesis adapted to face the body of the user and an air cushion is formed within said at least one layer between the slab of phase change material and the remainder of said at least one layer.

* * * * *